(12) United States Patent
Hoyte

(10) Patent No.: US 6,646,741 B1
(45) Date of Patent: Nov. 11, 2003

(54) METHOD AND APPARATUS FOR VISUALIZING PARTICLES SUSPENDED IN A FLUID

(75) Inventor: John M Hoyte, Bellingham, WA (US)

(73) Assignee: Spectrex Corporation, Redwood City, CA (US)

( * ) Notice: Subject to any disclaimer, the term of this patent is extended or adjusted under 35 U.S.C. 154(b) by 0 days.

(21) Appl. No.: 10/155,742

(22) Filed: May 24, 2002

(51) Int. Cl.[7] .............................................. G01N 21/00
(52) U.S. Cl. ...................................................... 356/338
(58) Field of Search ................................. 356/336, 338, 356/331, 442

(56) References Cited

U.S. PATENT DOCUMENTS

| | | | |
|---|---|---|---|
| 3,858,851 A | 1/1975 | Ogle | |
| 3,956,616 A | 5/1976 | Knollenberg | |
| 3,967,901 A | * 7/1976 | Rodriguez | 356/338 |
| 4,011,459 A | 3/1977 | Knollenberg et al. | |
| 4,363,551 A | * 12/1982 | Achter et al. | 356/338 |
| 4,623,252 A | 11/1986 | Hollenbeck | |
| 6,414,754 B1 | * 7/2002 | Johnson | 356/338 |

* cited by examiner

Primary Examiner—Michael P. Stafira
(74) Attorney, Agent, or Firm—Fenwick & West LLP

(57) ABSTRACT

Apparatus and method for direct visualization of particles suspended in a fluid medium include a source of a collimated beam of light that illuminates a sample volume of particles and reference volume of particles of a selected size and density. Light scattered from the particles is viewed directly along an axis skewed from the beams for comparatively assessing approximate particle size and density in the sample volume.

12 Claims, 3 Drawing Sheets

METHOD AND APPARATUS FOR VISUALIZING PARTICLES SUSPENDED IN A FLUID

RELATED CASE

The subject matter of this application relates to the subject matter disclosed in U.S. Pat. No. 4,623,252 entitled "Particulate Counter", issued on Nov. 18, 1986 to K. Hollenbeck, which is incorporated by reference herein in its entirety.

FIELD OF THE INVENTION

This invention relates to particle detection, and more particularly to apparatus and method for visualizing suspended particles in a fluid.

BACKGROUND OF THE INVENTION

Certain known apparatus for detecting particles suspended in a fluid such as water within a vessel commonly rely upon scattering of an incident beam of light in diverse directions off axis of the incident beam for various forms of optical detection at diverse angular positions about the axis of the incident beam (See, for example, U.S. Pat. Nos. 3,858,851 and 4,623,252). Such particle detection apparatus tends to rely upon elaborate optical detection schemes to implement quantifying and qualifying techniques used to determine the number and size of particles per unit volume. Accurate operation of such particle detection apparatus may be limited to sufficiently low particle density,or to sufficiently small size range of particles present in the fluid to avoid overloading or otherwise exceeding the detection and computational capabilities of such particle-detection apparatus. In such circumstances, pre-filtering or dilution processing of a test sample may be required in order to bring particle densities or particle size variations into operable ranges. In order to screen test samples for proper operational parameters a test sample may have to be previewed for conformance with operational limits of such elaborate particle detection apparatus in order to determine whether pre-filtering or dilution or other pre-test processing of a test sample may be required.

SUMMARY OF THE INVENTION

Accordingly, with illustrated embodiments of the present invention, a visualizing apparatus and method facilitate conducting quick initial visual evaluations of test samples for conformance with operational testing limits, or for other visual factors, with capability to provide approximate analyses of particle densities and particle sizes down to about one micron particle size in reliance upon only unaided eyesight of an operator. Embodiments of the apparatus and method include a collimated beam of light that is directed into a fluid sample along one axis, and include a viewing port aligned along a skewed axis for visualizing only light scattered from the incident light beam by suspended particles. The visualization axis for light thus scattered by suspended particles may be oriented with an orthogonal component aligned along the direction of light propagation of the incident light beam in order to facilitate viewing forwardscattered light from a test sample. Any portion of the incident light beam that traverses the fluid sample is absorbed at a location out of alignment with the skewed visualizing axis. The incident light beam may be repetitively scanned through the fluid sample along various paths in order to facilitate visualization of a maximum distribution of suspended particles throughout the fluid test sample. Similar scanning of an incident light beam through a population of reference samples positioned in close proximity to the test sample promotes rapid visual comparisons and estimations of sample sizes and densities via comparative visualizations through the viewing port of scattered light from both reference sample and test sample.

DETAILED DESCRIPTION OF THE INVENTION

Figure 1:
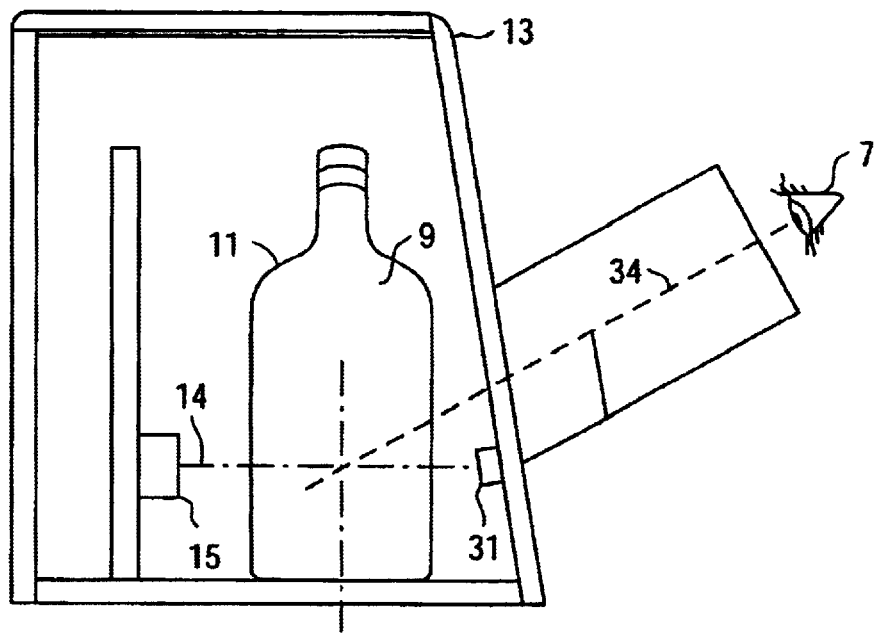
FIG. 1 is a pictorial side view of an embodiment of the present invention.
Figure 4:
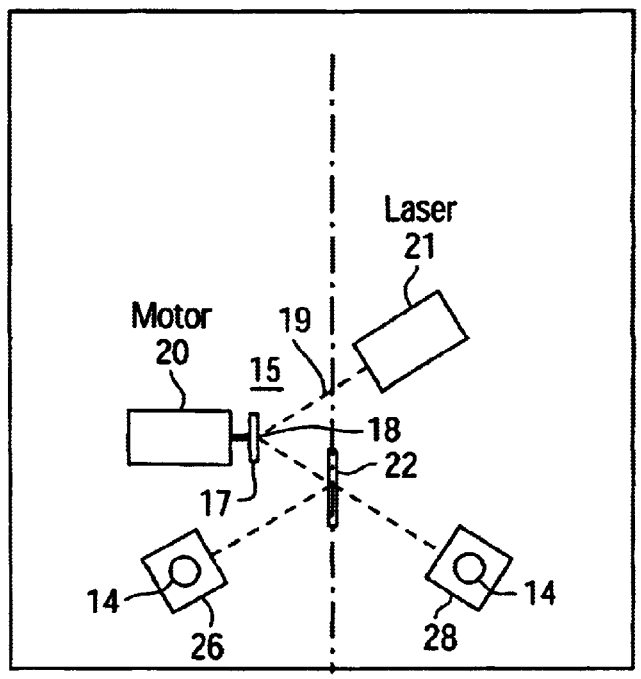
FIG. 4 is a pictorial plan view of a laser diode as one light source for the embodiment of FIG. 1.

Referring now to FIG. 1, there is shown a pictorial side view of an embodiment of the particle-visualizing apparatus according to the present invention. In this fundamental embodiment a fluid test sample 9 containing particles suspended in liquid such as water, alcohol, or oil, or the like, is contained within a suitable vessel such as a vial or bottle 11, and is positioned within a housing 13 in transverse alignment with a collimated beam 14 of light from a scanning source 15, as illustrated and described later herein with reference to FIG. 4. Alternatively, particles dispersed within a flowing stream of air may be contained within a transparent tube (not shown) that passes through the housing in transverse alignment with the beam 14 of light substantially in the position and orientation within the housing 13 as illustrated for a transparent vial or bottle 11. Such container or vessel may be rigid or flexible, glass or plastic, that is formed to desired standard dimensions (e.g., about 1–2.5 inches in diameter, or dimension through opposite walls), and may be clear and colorless or with color that may complement the color of the light beam for enhanced visual detection of particles. The scanning source of light 15, as illustrated in FIG. 4, may include a spinning wheel 17 that includes a mirrored surface 18 mounted in slightly non-perpendicular alignment with the shaft of motor 20 to receive an incident beam 19 from a light source 21 such as a low-power solid-state laser. The incident beam 19 reflects from mirror 18 along a circular path through beam splitter 22. The split beams then reflect off respective mirrors 26, 28 to produce scanning beams of light 14 in a selected circular cross section oriented, at least through the test sample 9 and, optionally, additionally through one or more reference samples positioned in close, spaced relationship to the test sample within the housing 13. The housing 13 may include doors or other portals to facilitate placement and removal of test and reference vessels at selected positions within the housing 13 to intercept a scanning beam 14.

Alternatively, as illustrated in FIG. 1, the beam of light from source 15 may be reflected from a rotating or oscillating mirror that is arranged to direct a collimated beam of light along another selected cross-sectional scan or path (e.g. horizontal sweep) through the test sample 9. Additionally, the companion beam may be similarly scanned through a reference sample 36 in closely-spaced position adjacent the test sample 9 within the housing 13 as illustrated in FIG. 2a, to facilitate comparative visualization by an observer 7 under substantially similar illumination conditions.

Figures 5A, 5B:
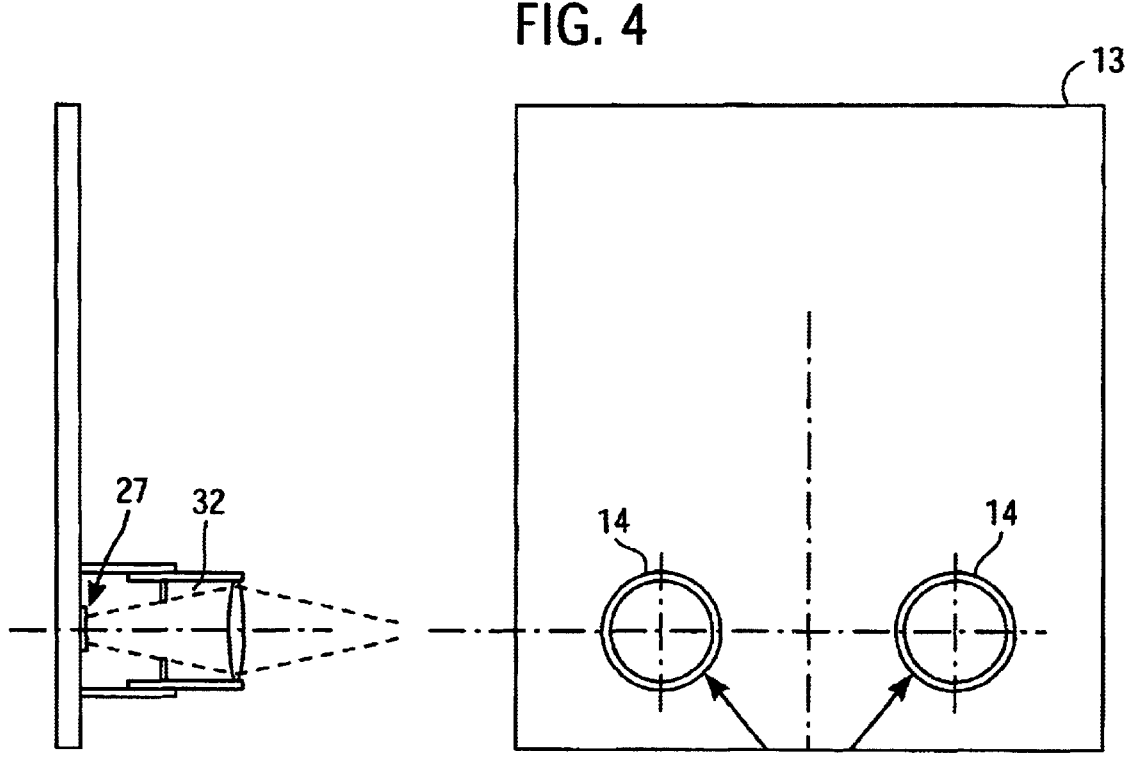
FIGS. 5a and 5b are side and plan views, respectively, of a light-emitting diode as another light source for the embodiment of FIG. 1.

The scanning light beam 14 may be initially collimated using a suitable lens system 32 from an incoherent light source such as a filament lamp or light-emitting diode 27, as illustrated in the side and plans views of FIGS. 5a, 5b.

The low-power solid-state laser 21 having optical power typically not greater than about 5 milliwatts may be disposed, as illustrated in FIG. 4, to supply the collimated coherent beam 14 of light to the scanning mechanism 15, 17–20 which then reflects the beam through at least the test sample or, optionally, additionally through the reference sample in the manner as previously described herein with reference to FIG. 1. Absorptive optical targets 31 are disposed on an inside wall of the housing 13 to receive any portion of the illuminating beam which passes through the test-sample or reference-sample vessels. These absorptive targets 31 inhibit reflected beams from re-entering the test sample and reference sample from a portion of the vessel wall opposite the portion of the vessel wall through which the incident swept beams 14 enters such samples 9, 36.

Figures 2A, 2B:
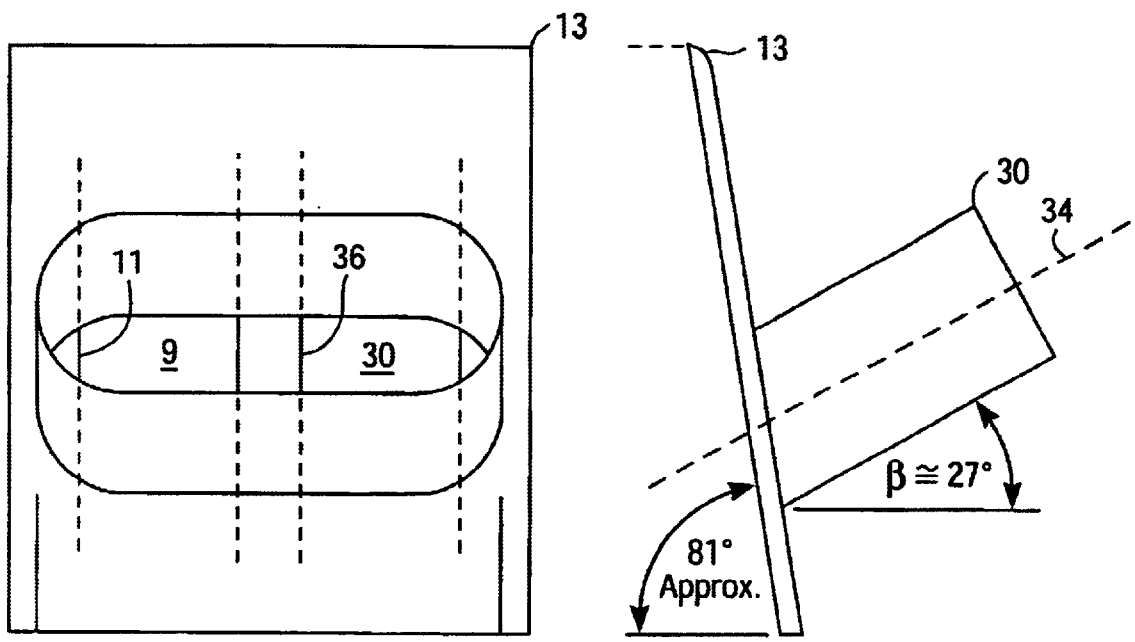
FIGS. 2a and 2b are front and side views, respectively, of the viewing port in the embodiment of FIG. 1.

In accordance with the present invention, a viewing port 30 is disposed on the housing 13, as illustrated in the front and side views of FIGS. 2a, 2b, to provide visualization of the test sample 9 and reference sample 36 within the housing 13 along an axis 34 and plane that is skewed from alignment with the axis and plane (or circular segment) of the swept beam 14. In this way, an observer 7 is protected from looking directly into any remaining portion of an illuminating beam 14 that passes through a test vessel 11 or reference vessel 36, and is limited to visualizing only the scattered light emanating from particles in the fluid medium within the test and reference vessels. The skewed orientation of the visualizing axis 34 or plane relative to the axis or plane of the swept incident beam 14 is preferably an acute angle β that is not greater than about 45° and not less than about 5°; and preferably is about 27° for optimal viewing of scattered light and adequate protection from directly viewing remaining portions of the swept beams that pass through the test and reference vessels 11, 36. In this configuration, it has been determined that an observer can detect the presence of suspended particles within a test sample 9 down to about 1 micron size without a viewing aid of a magnifier or lens system. A trained observer may therefore readily make visual comparisons of sizes and densities of particles in a test sample by visually comparing the light patterns produced thereby with the light patterns produced by one or more of a population of various reference samples 36 having calibrated different particle sizes and densities to serve as visual standards for the comparisons. In this way, approximations of particle sizes and densities in test samples 9 can be quickly and inexpensively determined, for example, as indicia of need for further pre-test processing of a sample, for example, via filtering or diluting in order to conform to density or particle size limitations suitable for more accurate quantitative analyses in particle counters or other particle detection apparatus.

Figure 3:
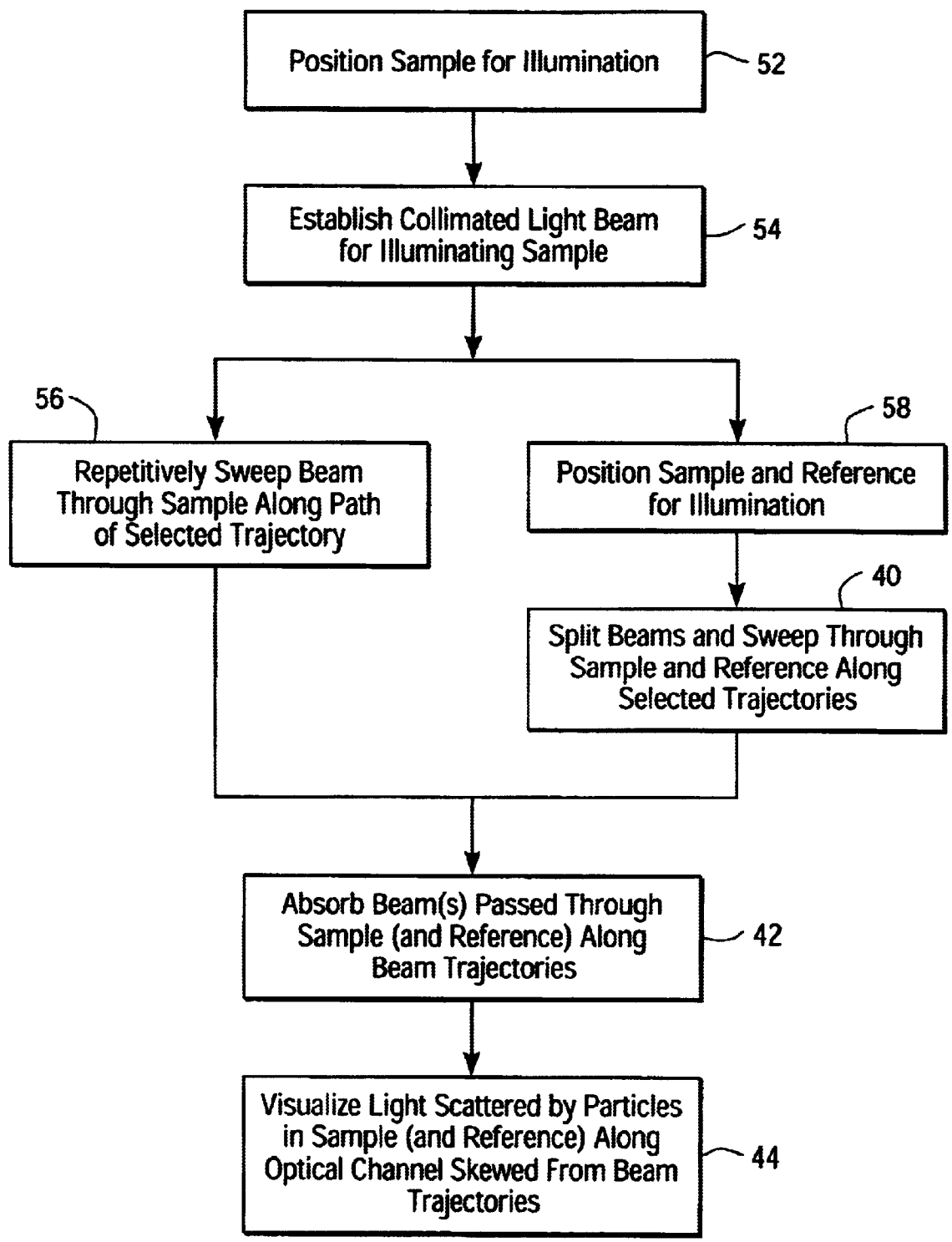
FIG. 3 is a flow chart illustrating a process embodiment of the present invention.

In operation, as illustrated in the flow chart of FIG. 3, the sample of particles suspended in a fluid medium (i.e., flowing air stream or liquid medium) is positioned 52 within the housing 13 to be illuminated by a beam of light. The test sample (and a reference sample) containing particles in a liquid may be swirled initially (or continually) to enhance statistical probabilities of scanning through particles present in the volume being scanned. The scanning beam of light is collimated 54 by a suitable lens system from an incoherent light source such as a filament lamp, or is collimated from a coherent light source such as a laser, as previously described herein. The scanning beam is repetitively swept 56 through the sample along a selected trajectory such as within a plane or about a circular path, or other scanning pattern, to scan through particles that are present in the fluid medium within a portion of the sample volume that is much larger than the cross section of the light beam alone.

Optionally, one or more of a population of particle references having different particle sizes and particle densities per unit volume of, for example, a liquid medium may be positioned 58 in close proximity to the particle sample within the housing 13. In this optional operating mode, the light beam is split (or is otherwise duplicated) for repetitive sweeps 40 through both the sample particles and reference particles along similar trajectories or paths. Any remaining portions of the beam or beams that pass through the sample particles (and reference particles) are absorbed 42 to suppress objectionable reflections back into the sample particles (and reference particles), for example, by absorptive optical targets 31 disposed within the housing 13 on opposite sides of the sample-particle and reference-particle vessels from the incident-beam sides thereof.

Thus, light scattered by sample particles (and reference particles) can be visualized 44 along an optical channel 34 that is skewed at an acute angle relative to axes of the trajectories of the sweeping light beams 14. In the absence of any lenses or magnifiers in the viewing channel, particle sizes can be readily discerned in sizes down to about 1 micron with unaided eyesight for rapid comparative visual analyses of densities and sizes of particles in the sample against one or more vessels of reference particles.

Therefore, the apparatus and process according to the present invention promotes direct visual assessments of particle sizes and densities of particulates suspended within a fluid medium, and such visual assessments can be enhanced by simultaneous illumination of test and reference samples within a common view port. In this way, corresponding visual patterns can be readily discerned by a trained observer to provide close approximations of applicable parameters among test and reference samples.

What is claimed is:

1. Apparatus for illuminating particles suspended within a fluid medium, comprising:

a housing for containing a volume of a sample including particles to be illuminated, and including a view port;

a source of illumination oriented to produce a beam of substantially collimated light through a portion of the volume of a sample;

a scanner disposed in the beam of light from the source for deflecting light therefrom recurringly through said portion of the volume along a substantially continuous path;

the view port in the housing being disposed along an axis skewed relative to the beam of light for channeling visualization of light scattered by particles within the portion of the volume of the sample; and an optical target disposed within the housing at a location in alignment with the beam of light on a side of the volume opposite the source of illumination and displaced from the view port for absorbing a portion of the beam of light that passes through the portion of the volume.

2. Apparatus according to claim 1 in which the substantially continuous path includes substantially circular rotational orientation of the beam through the portion of the volume of the sample.

3. Apparatus according to claim 1 in which the substantially continuous path includes a substantially planar orientation of the beam through the portion of the volume of the sample.

4. Apparatus for illuminating particles suspended within a fluid medium, comprising:

a housing for containing a volume of a sample including particles to be illuminated and a volume of reference particles suspended in a fluid medium and positioned in proximity to the volume of the sample, the housing including a view port;

a source of illumination oriented to produce a beam of substantially collimated light through a portion of the sample volume and through a portion of the reference volume;

the view port in the housing being disposed along an axis skewed relative to the beam of light for channeling visualization of light scattered by particles within the portions of the sample volume and reference volume; and an optical target disposed within the housing at a location in alignment with the beam of light on a side of the volumes opposite the source of illumination and displaced from the view port for absorbing portions of the beam of light that pass through the sample volume and through the reference volume.

5. Apparatus according to claim 1 in which the housing is disposed to receive the reference volume as selected ones of a population of a plurality of vessels containing liquid and reference particles therein of selected different sizes and particle densities per vessel.

6. Apparatus according to claim 1 including a scanner disposed in the beam of light from the source for deflecting light therefrom recurringly along the substantially continuous path through the portions of the sample and reference volumes.

7. Apparatus according to claim 6 in which the substantially continuous path includes substantially planar orientation of the beams through the portions of the sample and reference volumes.

8. Apparatus according to claim 6 including an optical splitter disposed within the beam of light for forming a plural number of beams oriented to illuminate the portions of the sample and reference volumes along substantially continuous paths therethrough.

9. Apparatus according to claim 8 in which each of the plural number of beams sweeps through a substantially continuously circular path through each of corresponding portions of the sample and reference volumes.

10. Apparatus according to claim 8 in which each of the plural number of beams sweeps through a substantially continuous planar path through each of corresponding portions of the sample and reference volumes.

11. A method for illuminating particles suspended in a fluid medium, comprising:

confining a sample volume of the fluid medium and particles;

confining a reference volume of particles in a fluid medium near the sample volume;

illuminating the sample and reference volumes with beams of light along substantially continuous paths through each of the volumes;

absorbing portions of the beams of light that pass through the sample volume and through the reference volume; and directly viewing light scattered from particles in the sample volume and in the reference volume along an axis skewed by a selected angle from the axis of the light beam.

12. The method according to claim 11 including:

directly comparably viewing light scattered from particles in a liquid medium within the sample volume with light scattered from particles in selected ones of a population of a plurality of reference volumes each containing different sizes and densities of particles suspended in a liquid medium.

* * * * *

UNITED STATES PATENT AND TRADEMARK OFFICE
CERTIFICATE OF CORRECTION

PATENT NO.    : 6,646,741 B1  Page 1 of 1
DATED         : November 11, 2003
INVENTOR(S)   : John M. Hoyte It is certified that error appears in the above-identified patent and that said Letters Patent is hereby corrected as shown below:

<u>Column 5,</u>
Lines 28 and 33, after the word "claim" delete "1", and insert -- 4 --

Signed and Sealed this

Second Day of March, 2004

JON W. DUDAS
*Acting Director of the United States Patent and Trademark Office*